(12) United States Patent
Kuhn et al.

(10) Patent No.: US 7,662,148 B2
(45) Date of Patent: Feb. 16, 2010

(54) SYSTEMS AND METHODS FOR INTRASTROMAL SCANNING PATTERNS

(75) Inventors: Tobias Kuhn, Heidelberg (DE); Frieder Loesel, Mannheim (DE)

(73) Assignee: Technolas Perfect Vision GmbH, Munich (DE)

( * ) Notice: Subject to any disclaimer, the term of this patent is extended or adjusted under 35 U.S.C. 154(b) by 1380 days.

(21) Appl. No.: 10/987,542

(22) Filed: Nov. 12, 2004

(65) Prior Publication Data
US 2006/0106372 A1 May 18, 2006

(51) Int. Cl.
*A61F 9/008* (2006.01)
(52) U.S. Cl. .......................................... 606/5; 128/898
(58) Field of Classification Search ............... 606/4–5
See application file for complete search history.

(56) References Cited

U.S. PATENT DOCUMENTS

| | | | |
|---|---|---|---|
| 3,769,963 A | 11/1973 | Goldman et al. | |
| 4,391,275 A | 7/1983 | Fankhauser et al. | |
| 4,665,913 A | 5/1987 | L'Esperance, Jr. | |
| 4,669,466 A | 6/1987 | L'Esperance | |
| 4,732,148 A | 3/1988 | L'Esperance, Jr. | |
| 4,770,172 A | 9/1988 | L'Esperance, Jr. | |
| 4,773,414 A | 9/1988 | L'Esperance, Jr. | |
| 4,941,093 A | 7/1990 | Marshall et al. | |
| 4,988,348 A | 1/1991 | Bille | |
| 5,549,632 A | 8/1996 | Lai | |
| 5,984,916 A | 11/1999 | Lai | |
| 5,993,438 A * | 11/1999 | Juhasz et al. | 606/5 |
| 6,010,497 A | 1/2000 | Tang et al. | |
| 6,325,792 B1 | 12/2001 | Swinger et al. | |
| 6,610,051 B2 | 8/2003 | Bille | |
| 2003/0212387 A1 | 11/2003 | Kurtz et al. | |

OTHER PUBLICATIONS

Heisterkamp et al., "Intrastromal Refractive Surgery With Ultrashort Laser Pulses: In Vivo Study On The Rabbit Eye", Laboratory Investigation, (2002), pp. 511-515.
Juhasz, et al., "Corneal Refractive Surgery With Femtosecond Lasers", IEEE Journal of Selected Topics In Quantum Electronics, (Jul./Aug. 1999), vol. 5, No. 4.
Juhasz, et al., "Time-Resolved Observations of Shock Waves and Cavitation Bubbles Generated by Femtosecond Laser Pulses in Corneal Tissue and Water", Lasers in Surgery and Medicine, 19:23-31, (1996).
Ratkay-Traub, et al., "First Clinical Results With the Femtosecond Neodynium-glass Laser in Refractive Surgery", Journal of Refractive Surgery, 19:94-103, (2003).

* cited by examiner

*Primary Examiner*—Henry M. Johnson, III
*Assistant Examiner*—Laurie Winslow
(74) *Attorney, Agent, or Firm*—Nydegger & Associates

(57) ABSTRACT

A method for photodisrupting a preselected subsurface volume of corneal tissue to alter a cornea's refractive properties is disclosed. Specifically, at least one stromal volume having a substantially conical shaped surface is photodisrupted. For this purpose, a laser device having a laser source, laser scanner and one or more optical elements is typically used. In one embodiment, a plurality of stromal volumes, with each stromal volume having a substantially conical shaped surface, is sequentially photodisrupted to form a contiguous stromal cavity. In a particular implementation, each conical shaped surface defines a cone axis that is aligned to be co-linear with a reference axis that passes through the anterior surface of the eye and may be aligned orthogonally to the anterior surface of the eye.

17 Claims, 2 Drawing Sheets

SYSTEMS AND METHODS FOR INTRASTROMAL SCANNING PATTERNS

FIELD OF THE INVENTION

The present invention pertains generally to ophthalmic laser surgery techniques. More particularly, the present invention pertains to devices and methods for photodisrupting a preselected, subsurface volume of corneal tissue. The present invention is particularly, but not exclusively, useful for removing a volume of stromal tissue from a cornea to correct the cornea's refractive properties.

BACKGROUND OF THE INVENTION

In the widely performed Laser In-Situ Keratomeleusis (LASIK) procedure, a microkeratome is used to incise the cornea of a patient and create a flap. The flap is then lifted to expose a bed of stromal tissue which is subsequently ablated using an Excimer laser. After ablation, the flap is replaced and allowed to heal. This process, although being somewhat successful in correcting vision deficiencies, has several drawbacks. For example, the creation of a suitable flap for a LASIK procedure is labor intensive and relies heavily on the skill and eye-hand coordination of the surgeon. In addition, the use of a microkeratome often produces an irregular incision which can create vision defects when the irregular, inner flap surface is replaced over a relatively smooth bed of ablated tissue.

As an alternative to corneal reshaping using LASIK, a train of laser pulses having relatively short pulse durations can be directed to a focal point at a predetermined subsurface location within a patient's cornea. This focal point can then be used to photodisrupt tissue at the focal point with precision and accuracy. For example, infrared pulses can be passed through corneal tissue with minimal energy loss to a subsurface focal point. An example of a procedure that uses a pulsed laser beam that is focused to a predetermined, subsurface location within a patient's cornea is disclosed in U.S. Pat. No. 4,907,586, which issued to Bille et al. for an invention entitled "Method for Reshaping the Eye".

In greater detail, the photodisruption of tissue by a pulsed laser results from a process termed "laser induced optical breakdown" (LIOB). Specifically, in the LIOB process, tissue breakdown occurs in the laser focus due to the extremely high, local electrical field that is generated. This high electric field exceeds the electron binding energy of the tissue atoms, and results in the generation of a microplasma, shockwaves and a cavitation bubble. Typically, the vaporized tissue diffuses out of the cornea within about 30-60 minutes. Importantly, the cavitation bubble created at each focal point collapses under intraocular pressure. As a consequence, this process can be used to effectively reshape the cornea.

When considering the use of subsurface photoablation for corneal reshaping, a general knowledge of the anatomy of the cornea is helpful. In detail, the cornea consists of several layers of tissue which are structurally distinguishable. In order, going in a posterior direction from outside the eye toward the inside of the eye, the various layers of a cornea are: an epithelial layer, Bowman's membrane, the stroma, Descemet's membrane, and an endothelial layer. Of these various structures, the stroma is the most extensive and is generally around four hundred microns thick. For this reason, stromal tissue is generally selected for removal in a refractive correction procedure.

Considering the stroma in further detail, it is generally comprised of around two hundred identifiable and distinguishable layers of lamellae. Each of these layers of lamellae in the stroma is somewhat dome-shaped, like the cornea itself, and they each extend across a circular area having a diameter of about nine millimeters. Each layer includes several lamellae. Unlike the entire layer that a particular lamella is in, each lamella in the layer extends through a shorter distance of only about one tenth of a millimeter (0.1 mm) to one and one half millimeters (1.5 mm). Finally, it is to be noted that, in a direction perpendicular to the layer, each individual lamella is only about two microns thick.

Within the general structure described above, it is to be appreciated that the stroma is considerably anisotropic. Specifically, the strength of tissue within a lamella is approximately fifty times the strength that is provided by the adhesive tissue that holds the layers of lamella together. Due to this relationship between strength and direction in the stroma, it is more efficient to photodisrupt tissue in volumes that extend orthogonally to the lamella layers than it is to photodisrupt tissue in volumes which extend along the lamella layers.

In addition to the considerations described above, another factor that can affect the efficiency and accuracy of a photodisruption procedure is the optical path that the laser takes to reach a focal point at a targeted location. In this regard, it can be appreciated that if the laser must pass through a previously photodisrupted location, the beam can become distorted. This unwanted distortion can affect both the location and size of the focal point and lead to inaccurate results.

In light of the above, it is an object of the present invention to provide devices and methods for photodisrupting stromal volumes having shapes which extend generally normal to the direction of the lamella layers. It is another object of the present invention to provide devices and methods for photodisrupting preselected stromal volumes which avoids placing the surgical laser on a beam path that passes through a previously photodisrupted location to reach a targeted location. Yet another object of the present invention is to provide devices and methods for correcting the refractive properties of a cornea which are easy to use, relatively simple to implement, and comparatively cost effective.

SUMMARY OF THE INVENTION

The present invention is directed to devices and methods for photodisrupting a preselected volume of corneal tissue. In a particular embodiment, a volume of stromal tissue is vaporized using a pulsed, infrared laser beam that is focused to a subsurface location in the stroma. In one application of the invention, a vision deficiency (e.g. myopia, hyperopia, etc.) can be corrected by vaporizing a preselected volume of corneal tissue to create a contiguous cavity within the stroma. When the cavity collapses under intraocular pressure, the cornea assumes a new shape and curvature.

In one aspect of the invention, a method is disclosed which begins by identifying the coordinates for each of a plurality of stromal locations. Specifically, the stromal locations are selected such that photodisruption at each location results in the photodisruption of a stromal volume that is bounded by two substantially parallel conical shaped surfaces that mutually define a cone axis. With these coordinates identified, the pulsed laser beam is brought to a focus at an initial, stromal location to photodisrupt tissue there. Next, the focal point is scanned along a predetermined path from one identified location to the next until photodisruption has occurred at all identified locations. For this purpose, a laser device having a laser source, laser scanner and one or more optical elements is typically used. In one exemplary setup, the laser device can include, in order, a laser source, a laser scanner for scanning in three dimensions, a plurality of lenses arranged as a telescope, a mirror, and a cutting lens. For some procedures, a contact lens can be used to stabilize the cornea relative to the laser source and conform the anterior surface of the eye to a preselected radius of curvature, R.

In one implementation of the invention, a plurality of stromal volumes are sequentially photodisrupted to form a contiguous stromal cavity. For this implementation, each stromal volume is bounded by two substantially parallel conical shaped surfaces, respectively. For example, each stromal volume can be photodisrupted having substantially parallel surfaces that are each a portion of a respective cone. Moreover, each conical surface may only extend partially around the cone's axis. Stated another way, each cone surface may subtend an azimuthal angle, $\alpha$, about the cone axis that is less than three hundred sixty degrees ($\alpha$<360 degrees). Alternatively, the conical surface can extend completely around the cone's axis ($\alpha$=360 degrees).

In some cases, the surface includes the vertex of the cone and in other cases a surface of the stromal volume consists of a cone portion that is distanced from the cone's vertex. In each case, the surface generated can be selected as desired by the operator. In one particular implementation, each conical shaped surface defines a right circular cone having a cone axis that is aligned to be co-linear with a reference axis that passes through the anterior surface of the eye and is aligned orthogonally to the anterior surface.

As indicated above, photodisruption occurs along a predetermined path. In one implementation of the present invention, the predetermined path includes focal point displacements that can be characterized by displacement vectors having a nonzero azimuthal component relative to the reference axis. For this implementation, photodisruption proceeds generally from an initial focal point location to a final focal point location with the initial focal point location being positioned further from the anterior surface of the eye than the final focal point location. In some cases, this technique can be used to ensure that the surgical laser is not placed on a beam path that passes through a previously photodisrupted location to reach a targeted location.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
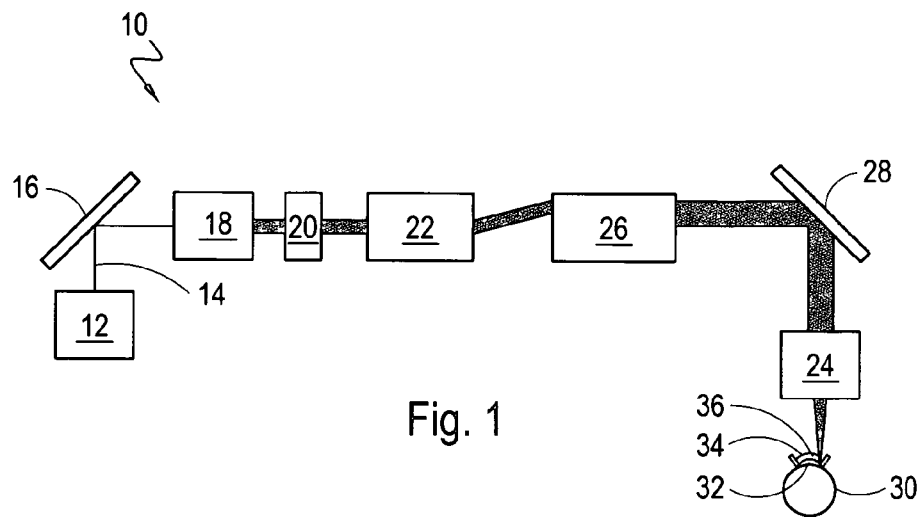
FIG. 1 is a schematic view showing the primary optical components of a system for photodisrupting a preselected volume of corneal tissue.

Referring initially to FIG. 1, an ophthalmic laser system for intrastromal subsurface photodisruption (by the effect of laser induced optical breakdown (LIOB)) is shown and generally designated 10. As shown in FIG. 1, the system 10 includes a laser source 12 for producing a pulsed laser beam and directing the laser beam along a first beam path 14. A typical embodiment of the laser source 12 includes an all solid-state, femtosecond (fs) laser with a pulse duration of 1 fs to about 100 ps, an operating wavelength in the near infrared and repetition rate in the range of 1 kHz to 1 Mhz.

Continuing with reference to FIG. 1, it can be seen that the laser beam generated at the laser source 12 is directed along the beam path 14 where it is reflected using a forty-five degree mirror 16. From the mirror 16, the beam is directed into a plurality of lenses that are arranged as a Galilei telescope 18. In the telescope 18, the laser beam is expanded and forwarded to the master shutter 20. The master shutter 20 acts as a safety element. After passing the shutter 20, the beam enters a scanning unit 22.

The scanning unit 22 includes means for three dimensional scanning of the laser beam. A more thorough description of a suitable scanning unit 22 and its operation is provided in co-pending, co-owned U.S. patent application Ser. No. 10/821,402, titled "Beam Steering System for Corneal Laser Surgery" and is hereby incorporated by reference in its entirety herein.

For the system 10, control signals are routed to a unit processor (not shown) where they are processed by, for example, a real-time operating system and evaluated by adequate hardware tools. If an error in laser output or positioning occurs during a procedure or calibration, the master shutter 20 is activated to block the beam to prevent any detrimental radiation from reaching the patient's eye.

Continuing with FIG. 1, it can be seen that after leaving the scanning unit 22, the beam is relayed to a cutting lens 24. Specifically, as shown, the beam passes first through a plurality of lenses 26 that are arranged as a telescope and is then reflected by a forty-five degree dichroic mirror 28. The dichroic mirror 28 permits the observation of the patient's eye 30 via a microscope (not shown) through the mirror 28 and cutting lens 24. It can also be seen that the system 10 includes a contact lens 34, which is typically made of transparent PMMA, to stabilize the cornea 32 relative to the cutting lens 24. Moreover, as shown, the contact lens 34 is positioned in contact with the cornea 32 to conform the anterior surface 36 of the cornea 32 with the contact lens 34. Typically, the conformed cornea 32 has a radius of curvature, R, in a range of between approximately 7.5 mm and approximately 11.0 mm. In most cases, a radius of curvature, R, of approximately 8.8 mm (which is close to the natural curvature of the cornea's exterior surface) is used.

The fixation and alignment of the patient's eye 30 is typically accomplished using the contact lens 34 and an alignment device (not shown). For this purpose, the contact lens 34 is applied to and held against the eye 30 using an eye stabilizing element (not shown) that is attached to, or is integral with, the contact lens 34. Once centered on the eye 30, the eye stabilizing element is fixed by applying a vacuum. Next, the alignment device is placed between the beam exit of the cutting lens 24 and the alignment device. Using a motorized patient chair, the eye 30 and the eye stabilizing element are moved towards the alignment device. The connection between the eye stabilizing element and the alignment device is self-centering to maintain a proper x-y alignment. Furthermore, the setup provides the correct "z" distance between the patient's eye 30 and the cutting lens 24. A pressure sensor (not shown) is used to measure the pressure on the eye 30 when the contact between the alignment device and the eye stabilizing element is established. A more thorough description of the fixation and alignment system and its operation is provided in co-pending, co-owned U.S. patent application Ser. No. 10/790,625, titled "System and Method for Positioning a Patient for Laser Surgery" and is hereby incorporated by reference in its entirety herein.

Figure 2:
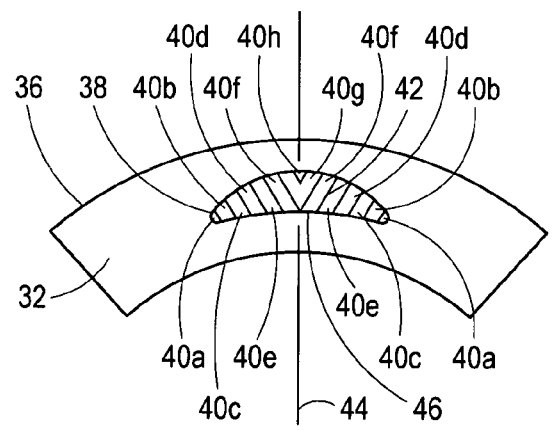
FIG. 2 is an enlarged cross-sectional view of a cornea that has been photodisrupted to create a lenticular shaped stromal cavity to alter the refractive properties of the cornea.

FIG. 2 shows a cornea 32 that has been photodisrupted to create a lenticular shaped stromal cavity 38. Although a lenticular shaped cavity 38 is shown, it is to be appreciated that the lenticular shape is merely exemplary and that the system 10 can be used to photodisrupt cavities having other non-lenticular shapes. FIG. 2 further illustrates that the cavity 38 is formed by the photoablation of eight stromal volumes 40a-h. As shown, each stromal volume 40 is formed having a substantially conical shaped surface, of which exemplary conical surface 42, which corresponds to volume 40e, has been labeled. In a typical procedure, these volumes 40a-h are sequentially photodisrupted to form the contiguous stromal cavity 38. For the cavity 38 shown, each stromal volume 40a-h has a surface that is a portion of a respective substantially circular cone having a cone axis that is co-linear with the optical axis 44 of the eye 30. It can be further seen that some volumes (e.g. volume 40g) include the vertex 46 of the cone while other volumes (e.g. volume 40b) consist only of a cone portion that is distanced from the cone's vertex. To create the cavity 38, the volumes 40 are typically photodisrupted in sequential order beginning with volume 40a and ending with volume 40h. Although not illustrated by FIG. 2, it is to be appreciated that some volumes (e.g. volume 40a) will typically be partially or fully collapsed during the photodisruption of volume 40h.

Figure 3:
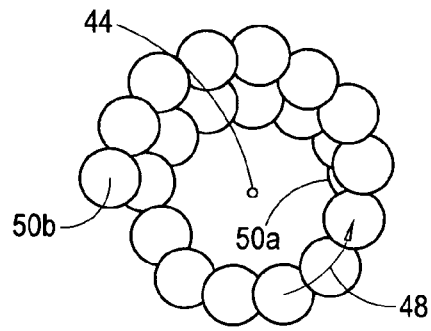
FIG. 3 is a schematic diagram illustrating a focal point path through the stroma.

As shown in FIG. 3, within each volume 40a-h, photodisruption occurs along a predetermined path. Typically, as shown in FIG. 3, the predetermined path can include focal point displacements that can be characterized by displacement vectors having a nonzero azimuthal component relative to the optical axis 44. For this implementation, photodisruption proceeds generally in the direction of arrow 48 from a relatively posterior focal point 50a to a relatively anterior focal point 50b. This technique can be used to ensure that the surgical laser is not placed on a beam path that passes through a previously photodisrupted location to reach a targeted location.

Figure 4:
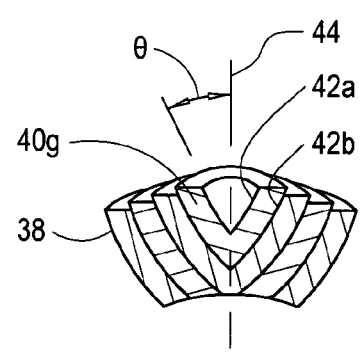
FIG. 4 is a perspective view of a photodisrupted stromal cavity in partial cross section to show the conical shaped surfaces created by the present methods.

FIG. 4 shows another view of a portion of the lenticular shaped stromal cavity 38 that has been photodisrupted. From FIG. 4, it can be seen the volume 40g is bounded by two substantially parallel conical shaped surfaces 42a,b. Moreover, FIG. 4 shows that these conical shaped surfaces 42a,b mutually define a cone axis 44. As further shown, surface 42a is part of a right circular cone having a cone angle, θ, that is between about 0 degrees and 50 degrees. It happens that for a treatment diameter of about 12 mm, the angle, θ, will be equal to about forty degrees (θ=40°).

Figure 5:
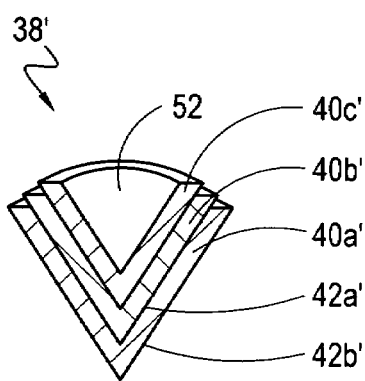
FIG. 5 is a perspective view of another photodisrupted stromal cavity in partial cross section to show the conical shaped surfaces created by the present methods.
Figure 6:
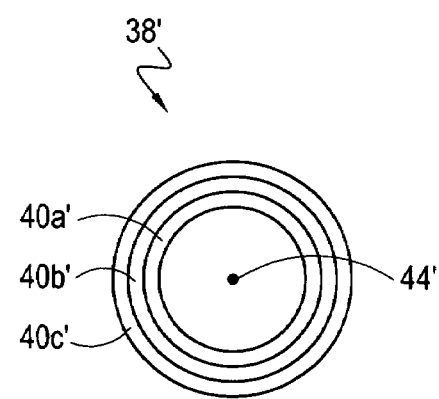
FIG. 6 is a top view of the photodisrupted stromal cavity shown in FIG. 5.

FIGS. 5 and 6 show another stromal cavity (designated cavity 38') having volumes 40a'-40c'. As shown, for the stromal cavity 38', each volume 40a'-40c' is bounded by two substantially parallel conical shaped surfaces. For example, volume 40a' is bounded by conical shaped surfaces 42a' and 42b'. It can be further seen that the conical shaped surfaces for each volume 40a'-40c' include the conical vertex for their respective cones. In addition, as best seen in FIG. 6, each of the volumes 40a'-40c' extend completely around the cone axis 44'. Also, it can be seen in FIG. 5 that the cavity 38' surrounds a conical shaped, non-ablated volume 52.

Figure 7:
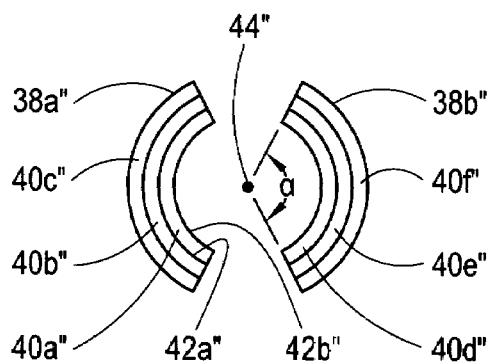
FIG. 7 is a top view of the photodisrupted stromal cavity in which conical surfaces are created that subtend an azimuthal angle about a cone axis of less than one-hundred eighty degrees.

FIG. 7 illustrates yet another example of an ablation pattern having two stromal cavities (designated cavity 38a" and cavity 38b"). FIG. 7 shows that cavity 38a" includes volumes 40a"-40c" and cavity 38b" includes volumes 40d"-40f". For the stromal cavities 38a" and 38b", each volume 40a"-40f" is bounded by two respective, substantially parallel conical shaped surfaces. For example, volume 40a" is bounded by conical shaped surfaces 42a" and 42b". Unlike the embodiment shown in FIG. 6, however, for the stromal cavities 38a" and 38b", each volume 40a"-40f" has a pair of conical shaped surfaces with each conical shaped surface subtending an azimuthal angle, α, about a cone axis 44" that is less than one-hundred eighty degrees, as shown. Thus, each volume 40a"-40f" does not extend completely around the cone axis 44". In one implementation, the entire cavity 38a" is ablated followed by ablation of the cavity 38b". Alternatively, the ablation pattern shown in FIG. 7 can be ablated with ON-OFF, full circle raster scans. In this manner, the cavities 38a", 38b" are ablated by sequentially ablating volumes in the following order: volume 40a", volume 40d", volume 40b", volume 40e", volume 40c" and then volume 40f".

While the particular Systems and Methods for Intrastromal Scanning Patterns as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A method for intrastromal refractive treatment of an eye, the eye having an anterior surface and a stroma, the method comprising the steps of:

establishing a frame of reference for the eye, wherein the frame of reference includes a reference axis passing through the anterior surface of the eye and aligned substantially orthogonally thereto;

directing a laser beam to a subsurface focal point in the stroma at a radial distance from the reference axis to photodisrupt stromal tissue at the focal point; and scanning the subsurface focal point along a predetermined path to photodisrupt a stromal volume, wherein the stromal volume is bounded by substantially parallel conical shaped surfaces mutually defining a cone axis, with the cone axis being co-linear with the reference axis.

2. A method as recited in claim 1 wherein said conical shaped surfaces are a first conical shaped surface and a second conical shaped surface and said first conical shaped surface is a portion of a right circular cone.

3. A method as recited in claim 2 wherein the right circular cone defines a vertex and the first conical shaped surface includes the vertex.

4. A method as recited in claim 2 wherein the eye has an optical axis and the reference axis is substantially co-linear with the optical axis.

5. A method as recited in claim 2 wherein the right circular cone defines a cone angle and the cone angle is in the range of 0 degrees to 50 degrees.

6. A method as recited in claim 1 wherein the predetermined path includes focal point displacements characterized by displacement vectors having a nonzero component parallel to the reference axis.

7. A method as recited in claim 1 wherein the predetermined path includes focal point displacements characterized by displacement vectors having a nonzero azimuthal component relative to the reference axis.

8. A method as recited in claim 1 wherein stromal tissue is photodisrupted along the predetermined path at an initial focal point location and a final focal point location, and wherein the initial focal point location is positioned further from the anterior surface of the eye than the final focal point location.

9. A method as recited in claim 1 wherein the stromal volume is a first stromal volume and the method further comprises the step of scanning a focal point along a predetermined path to photodisrupt a second stromal volume, the second stromal volume having a substantially conical shaped surface.

10. A method as recited in claim 1 wherein said scanning step photodisrupts a plurality of stromal volumes to create a contiguous lenticular shaped cavity, and wherein each stromal volume is bounded by substantially parallel conical shaped surfaces mutually defining a cone axis, with the cone axis being co-linear with the reference axis.

11. A method of intrastromal refractive treatment for an eye, the eye having a stroma, the method comprising the steps of:

directing a laser beam to a subsurface focal point in the stroma to photodisrupt stromal tissue at the focal point;

scanning the focal point along a first predetermined path to photodisrupt a first stromal volume, the first stromal volume having a substantially first conical shaped surface; and moving the focal point along a second predetermined path to photodisrupt a second stromal volume, the second stromal volume having a substantially second conical shaped surface and being contiguous with the first stromal volume.

12. A method as recited in claim 11 wherein the substantially first conical shaped surface is a portion of a first right circular cone and the substantially second conical shaped surface is a portion of a second right circular cone.

13. A method as recited in claim 12 wherein the first right circular cone defines a vertex and the first conical shaped surface includes the vertex.

14. A method as recited in claim 12 wherein the eye has an optical axis, the first cone defines a first cone axis, the second cone defines a second cone axis, and wherein the first and second cone axes are co-linear with the optical axis.

15. A method as recited in claim 12 wherein the eye has an anterior surface and an optical axis, the first right circular cone defines a first vertex, the second right circular cone defines a second vertex, the scanning step is performed before the moving step, and wherein the first and second vertex are located on the optical axis with the first vertex located further from the anterior surface than the second vertex.

16. A method as recited in claim 15 wherein the second conical shaped surface includes the second vertex.

17. A method as recited in claim 11 wherein the substantially first and second conical shaped surface defines a cone axis and subtends an azimuthal angle, $\alpha$, about the cone axis of less than three hundred sixty degrees ($\alpha$<360 degrees).

* * * * *